(12) United States Patent
Troup et al.

(10) Patent No.: US 8,073,626 B2
(45) Date of Patent: Dec. 6, 2011

(54) BIOPOLYMER ARRAY READING

(75) Inventors: Charles D. Troup, Livermore, CA (US); Herbert F. Cattell, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 2342 days.

(21) Appl. No.: 10/355,571

(22) Filed: Jan. 31, 2003

(65) Prior Publication Data

US 2004/0152082 A1 Aug. 5, 2004

(51) Int. Cl.
*G01N 33/48* (2006.01)
*C12M 1/00* (2006.01)

(52) U.S. Cl. ...................... 702/19; 435/283.1

(58) Field of Classification Search ................. None
See application file for complete search history.

(56) References Cited

U.S. PATENT DOCUMENTS

| | | | |
|---|---|---|---|
| 5,275,951 A | 1/1994 | Chow et al. | |
| 5,281,540 A | 1/1994 | Merkh et al. | |
| 5,314,829 A | 5/1994 | Coles | |
| 5,404,523 A | 4/1995 | DellaFera et al. | |
| 5,795,714 A | 8/1998 | Cantor et al. | |
| 5,812,793 A | 9/1998 | Shakib et al. | |
| 5,837,454 A | 11/1998 | Cozzette et al. | |
| 6,136,274 A * | 10/2000 | Nova et al. | 422/102 |
| 6,169,992 B1 | 1/2001 | Beall et al. | |
| 6,180,351 B1 | 1/2001 | Cattell | |
| 6,215,894 B1 | 4/2001 | Zeleny et al. | |
| 6,372,428 B1 | 4/2002 | Nova et al. | |
| 6,406,849 B1 | 6/2002 | Dorsel et al. | |

FOREIGN PATENT DOCUMENTS

| | | |
|---|---|---|
| GB | 2319838 | 6/1998 |
| JP | 63223557 | 9/1998 |

* cited by examiner

*Primary Examiner* — Eric S Dejong

(57) ABSTRACT

A method for processing biopolymer arrays and apparatus and computer program products for executing the method. The method may include reading a different array identifier for each biopolymer array from a tag associated with that array. At least some of the biopolymer arrays are read and results from each read array saved in a memory linked with the read identifier for that array. Different communication addresses and a selection of an array identifier for each, are received. For at least some of the arrays, the saved results for each are matched with one of the different communication addresses using the identifier, and the saved results transmitted for those arrays to the matched different communication addresses. A method of processing data from the reading of biopolymer arrays is also provided.

25 Claims, 4 Drawing Sheets

BIOPOLYMER ARRAY READING

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Biopolymer arrays such as polynucleotide arrays (for example, DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers onto a substrate, or by in situ synthesis methods. The in situ fabrication methods include those described in U.S. Pat. No. 5,449,754 for synthesizing peptide arrays, and in U.S. Pat. No. 6,180,351 and WO 98/41531 and the references cited therein for synthesizing polynucleotide arrays. Further details of fabricating biopolymer arrays are described in U.S. Pat. No. 6,242,266, U.S. Pat. No. 6,232,072, U.S. Pat. No. 6,180,351, and U.S. Pat. No. 6,171,797. Other techniques for fabricating biopolymer arrays include known light directed synthesis techniques.

In array fabrication, the probes formed at each feature is usually are expensive. Additionally, sample quantities available for testing are usually also very small and it is therefore desirable to simultaneously test the same sample against a large number of different probes on an array. These conditions make it desirable to produce arrays with large numbers of very small (for example, in the range of tens or one or two hundred microns), closely spaced features (for example many thousands of features). After the arrays are exposed to a sample and read, the array reading apparatus must be able to read such arrays with a very fine resolution (for example, in the range of five to twenty microns). This requires an array reader which may be expensive and which may take some time to read each array. On the other hand, many users will not need to occupy such a reader full-time. Thus, to reduce per user costs many different users may send their arrays for reading to a same array reader. The read results for the users different arrays can be sent to a common computer to which each user may visit and retrieve the results for their array.

The present invention recognizes that it would be desirable to provide different users who use a common biopolymer array reader, with a convenient and easy to use way of obtaining the read results for their arrays or status of the reading of their arrays.

SUMMARY OF THE INVENTION

The present invention then, provides in one aspect a method of processing chemical arrays (such as biopolymer). This method includes reading a different array identifier for each array from a tag associated with that array. At least some of the biopolymer arrays are read and results saved from each read array in a memory linked with the read identifier for that array. Different communication addresses and a selection of an array identifier for each, are received. For at least some of the arrays, the present invention matches the saved results for each with one of the different communication addresses using the identifier, and communicating the saved results for those arrays to the matched different communication addresses. The method may be carried out at an array reading station.

In another aspect the present invention provides an array reading station for reading multiple biopolymer arrays. The array reading station includes an identifier reader to read a different array identifier for each biopolymer array from a tag associated with that array, an array reader which may be the same or different from the identifier reader, a memory unit, and a communications unit. There is further included a processing unit in communication with the identifier reader, array reader, and memory unit, such that a method of the present invention can be executed.

There is further provided by an aspect of the present invention, a method of processing data from the reading of biopolymer arrays. This method includes receiving results from reading each array with a linked read array identifier, and saving each read array result in a memory linked to the array identifier. Different communications addresses and a selection of an array identifier for each are also received. For at least some of the arrays, the saved results for each are matched with one of the different communication addresses using the identifier, and the saved results for those arrays transmitted to the matched different communication addresses.

The present invention further provides a computer program product which includes a computer readable medium carrying a computer program code which performs a method of the present invention. Also provided by the present invention is a method which includes transmitting a communication address and a selection of an array identifier, and receiving as a result of a method already described, the results from reading the array specified by that array identifier.

Different various aspects of the present invention can provide any one or more of the following or other useful benefits. For example, many users can have their different arrays read by the same array reader, and the results from reading or status on reading conveniently transmitted to the different communication addresses of the users based on the array identifier associated with the different arrays.

BRIEF DESCRIPTION OF THE DRAWINGS

Embodiments of the invention will now be described with reference to the following drawings in which:

FIG. 1 illustrates a substrate carrying multiple arrays, such as may be read by a method of the present invention;

FIG. 2 is an enlarged view of a portion of FIG. 2 showing multiple spots or features of one array; and FIG. 3 is an enlarged illustration of a portion of the substrate of FIG. 1;

Figure 4:
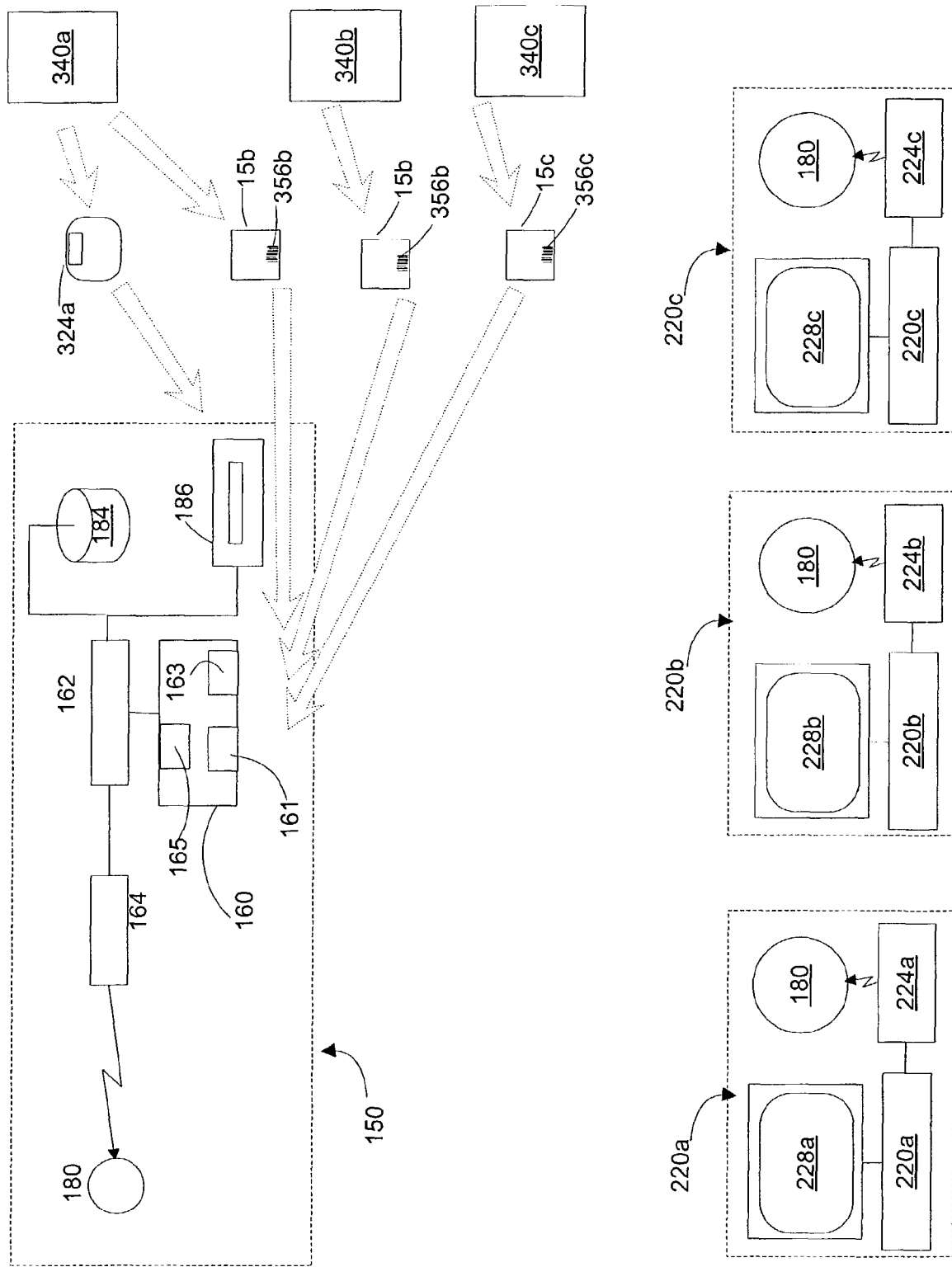
FIG. 4 illustrates an apparatus of the present invention and its use.

To facilitate understanding, identical reference numerals have been used, where practical, to designate the same elements which are common to different figures. Drawings are not necessarily to scale. Throughout this application any different members of a generic class may have the same reference number followed by different letters (for example, arrays 12a, 12b, 12c, and 12d may generically be referenced as "arrays 12")

DETAILED DESCRIPTION OF EMBODIMENTS OF THE INVENTION

Throughout the present application, unless a contrary intention appears, the following terms refer to the indicated characteristics.

A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

An "oligonucleotide" generally refers to a nucleotide multimer of about 10 to 100 nucleotides in length, while a "polynucleotide" includes a nucleotide multimer having any number of nucleotides.

An "array", unless a contrary intention appears, includes any one, two or three-dimensional arrangement of addressable regions bearing a particular chemical moiety or moieties (for example, biopolymers such as polynucleotide sequences) associated with that region. Each region may extend into a third dimension in the case where the substrate is porous while not having any substantial third dimension measurement (thickness) in the case where the substrate is non-porous. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). An array feature is generally homogenous and the features typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other).

An "array layout" or "array characteristics", refers to one or more physical, chemical or biological characteristics of the array, such as feature positioning, one or more feature dimensions, or some indication of an identity or function (for example, chemical or biological) of a moiety at a given location, or how the array should be handled (for example, conditions under which the array is exposed to a sample, or array reading specifications or controls following sample exposure).

"Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

When one item is indicated as being "remote" from another, this is referenced that the two items are at least in different buildings, and may be at least one mile, ten miles, or at least one hundred miles apart. When different items are indicated as being "local" to each other, they are at least in the same building and may be in the same room of a building. "Communicating", "transmitting" and the like, reference conveying data representing information as electrical or optical signals over a suitable communication channel (for example, a private or public network, wired, optical fiber, wireless, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item (for example, an array or array carrying package). When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that one unambiguously references the other. In particular, a tag can be associated with an array by being on the same substrate that carries the array or on or in a package or kit carrying the array. One item of data is "linked" to another when an input of one item unambiguously retrieves the other. In particular, when saved results from reading an array are "linked" with the read identifier for that array, then an input of the identifier into a processor which accesses a memory carrying the linked saved results unambiguously retrieves the saved results linked to that identifier.

A "processor" or "processing unit" references any combination of hardware or software which can control components as required to execute recited steps and includes. For example a processor or processor unit includes, for example, a general purpose digital microprocessor suitably programmed (for example, from a computer readable medium carrying necessary program code or by communication from a remote location) to perform all of the steps required of it, or any hardware or software combination which will perform those or equivalent steps.

A "memory" or "memory unit" refers to any device which can store information for retrieval by a processor, and may include magnetic, optical, or solid state memory devices. A memory or memory unit may have more than one actual memory device (for example, a memory may have multiple memory devices).

An array "assembly" may be the array plus only a substrate on which the array is deposited, although the assembly may be in the form of a package which includes other features (such as a housing with a chamber).

It will also be appreciated that throughout the present application, that words such as "front", "back", "top", "upper", and "lower" are used in a relative sense only.

"May" refers to optionally.

Any recited method can be carried out in the order of events recited or in any other order which is logically possible. Reference to a singular item, includes the possibility that there are plural of the same item present. All patents and other references cited in this application, are incorporated into this application by reference except insofar as anything in those patents or references, including definitions, conflicts with anything in the present application (in which case the present application is to prevail).

Methods of the present invention can additionally include, for each of at least some of the received selection of array identifiers, transmitting status information on array reading for the received array identifier to the received communication address for that identifier.

In methods of the present invention, the receiving of the communication addresses and selected array identifier for each may occur before the reading of the array specified by the identifier. In this case, the method may additionally include saving the different communication addresses and the selected array identifier for each in a memory. Following reading and saving of results and read array identifiers for the array specified by the received identifier, then the matching and transmission previously referenced may take place automatically.

Alternatively, the reading at least some of the biopolymer arrays and saving results from each read array in a memory linked with the read identifier for that array, may occur before the array identifier specifying that array and the communication address is received. In this case, the matching and transmitting previously referenced may be automatically performed following the receiving of a communication addresses and a selection of an array identifier which specifies the previously read array.

The tag may be associated with an array in various manners. For example, the tag may be on a same substrate carrying the array or on or in a same package as the array. Different types of tags are also possible. For example, the tag may be or include: a bar code or other optically readable device (for example, an optically readable memory); or an electrically readable memory.

Figures 1, 2, 3:
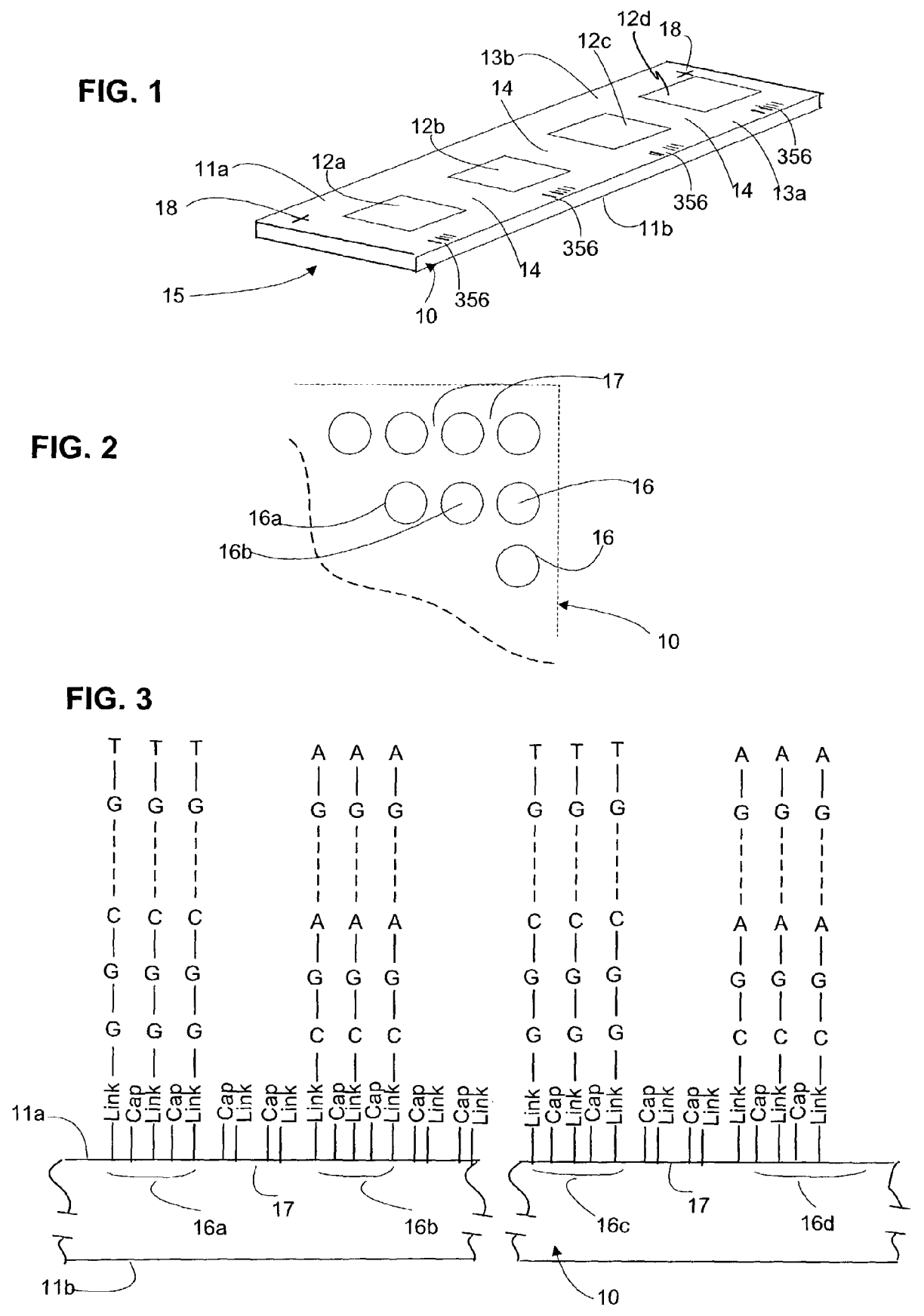

Referring now to FIGS. 1-3, an array assembly 15 (which may be referenced also as an "array unit") includes arrays 12 which may be read in methods of the present invention. Substrate 10 may also be in the form of an a rigid substrate 10 (for example, a transparent non-porous material such as glass or silica) of limited length, carrying one or more arrays 12 disposed along a front surface 11a of substrate 10 and separated by inter-array areas 14. Alternatively, substrate 10 can be flexible (such as a flexible web). The substrate may be of one material or of multi-layer construction. Substrate 10 is typically non-porous, and may be smooth or substantially planar, or have irregularities, such as depressions or elevations (although irregular substrate surfaces may make reading of the exposed array more difficult). A back side 11b of substrate 10 does not carry any arrays 12. The arrays on substrate 10 can be designed for testing against any type of sample, whether: a trial sample; reference sample; a combination of the foregoing; or a known mixture of polynucleotides, proteins, polysaccharides and the like (in which case the arrays may be composed of features carrying unknown sequences to be evaluated). While four arrays 12 are shown in FIG. 1, it will be understood that substrate 10 may use any number of desired arrays 12 such as at least one, two, five, ten, twenty, fifty, or one hundred (or even at least five hundred, one thousand, or at least three thousand). When more than one array 12 is present they may be arranged end to end along the lengthwise direction of substrate 10. Depending upon intended use, any or all of arrays 12 may be the same or different from one another and each will contain multiple spots or features 16 of biopolymers in the form of polynucleotides.

A typical array 12 may contain more than: ten, one hundred, one thousand, or ten thousand features. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature of the same composition are excluded, the remaining features may account for at least 5%, 10%, or 20% of the total number of features).

In any array 12 the features 16 may be spaced apart by a distance greater than 0 and less than 70%, 60% 50%, 25%, or 10% of a maximum dimension of the feature. Further, the features may have a maximum dimension of between 20 (or 50) to 100 (or 80) microns and are spaced apart by less than 130 microns (or by less than 100 or 50 microns). Various feature densities on the substrate surface are possible. For example, features having a maximum dimension greater than any of the foregoing figures may be present on the surface of at least 30 features/mm$^2$, 40 features/mm$^2$, or 60 features/mm$^2$. While round features 16 are shown, various other feature shapes are possible (such as elliptical). The features 16 may also be arranged in other configurations (for example, circular) rather than the rectilinear grid illustrated. Similarly, arrays 12 on a same substrate 10 need not be laid out in a linear configuration.

Each array 12 may cover an area of less than 100 cm$^2$, or even less than 50 cm$^2$, 10 cm$^2$ or 1 cm$^2$. In many embodiments, particularly when substrate 10 is rigid, it may be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. When substrate 10 is flexible, it may be of various lengths including at least 1 m, at least 2 m, or at least 5 m (or even at least 10 m). With arrays that are read by detecting fluorescence, the substrate 10 may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide. It will be appreciated though, that the interfeature areas 17 could be of various sizes and configurations. Each feature 16 carries a predetermined polynucleotide (which includes the possibility of mixtures of polynucleotides). As per usual, A, C, G, T represent the usual four nucleotides. "Link" (see FIG. 3 in particular) represents a linking agent (molecule) covalently bound to the front surface and a first nucleotide, as provided by a method of the present invention and as further described below. The Link serves to functionalize the surface for binding by the first nucleotide during the in situ process. "Cap" represents a capping agent. The Link may be any of the "second silanes" referenced in U.S. Pat. No. 6,444,268 while the Cap may be any of the "first silanes" in that patent. However, different linking layer compositions than those silanes could be used. As already mentioned, the foregoing patents are incorporated herein by reference, including for example the details of the linking layer compositions used therein.

Substrate 10 also has one or more identifiers 356 each in the form of a bar code. Each identifier is carried by a tag. The tag may be just a region of substrate 10 onto which the identifier is directly printed, labels attached to substrate 10 onto which the identifier are printed, a memory (for example, a solid state memory) attached to substrate 10 and which carries the identifier, a printed label or paper or a memory received in or on a same package as the substrate 10. Identifiers such as other optical or magnetic identifiers could be used instead of bar codes 356 which will carry the information discussed below. Each identifier may be associated with its corresponding array by being positioned adjacent that array 12 on the same substrate 10. However, this need not be the case and identifiers such as bar code 356 can be positioned elsewhere on substrate 10 if some other means of associating each bar code 356 with its corresponding array is provided (for example, by relative physical locations). Further, a single identifier might be provided which is associated with more than one array 12 on a same substrate 10 and such one or more identifiers may be positioned on a leading or trailing end of substrate 10. The substrate may further have one or more fiducial marks 18 for alignment purposes during array fabrication or reading.

FIGS. 2 and 3 illustrate ideal features 16 of an array 12 where the actual features formed are the same as the target (or "aim") features, with each feature 16 being uniform in shape, size and composition, and the features being regularly spaced. Such an array when fabricated by drop deposition methods, would require all reagent droplets for each feature to be uniform in shape and accurately deposited at the target feature location. In practice, such an ideal result may be difficult to obtain due to fixed and random errors during fabrication.

Arrays 12 may be fabricated by drop deposition methods such as described in U.S. Pat. No. 6,180,351, U.S. Pat. No. 6,242,266, U.S. Pat. No. 6,306,599, and U.S. Pat. No. 6,420,180. As mentioned above, the foregoing references are incorporated herein by reference particularly as relates to the in situ fabrication apparatus and methods disclosed therein. Alternatively, arrays 12 can be fabricated by known light directed synthesis methods.

Referring to FIG. 4, an apparatus of the present invention is illustrated in the form of an array reading station 150 for processing an array 12. Such a reading station 150 may be remote from a fabrication station at which the array to be processes was fabricated. The reading station 150 includes a memory 184, an array reader 160 which can read an array, data writer/reader 186, a communication module 164 which also has access to communication channel 180, and a processor 162 communicating with and controlling each of the foregoing. Data writer/reader 186 may be any suitable device which can at least read (and optionally also write onto) a portable magnetic, optical, or solid state memory (such as a magnetic diskette, optical CD or DVD disk, or memory chip). Communication module 164 may be any type of suitable communication module, such as a telephone modem, LAN or WAN card, satellite modem, optical modem, or otherwise. Processors 162 can be programmed from any computer readable medium carrying a suitable computer program. For example, such a medium can be a memory device read by writer/reader 186 or may be programmed from a remote location through communication channel 180. Array reader 160, processor 162, module 164, memory 184, and data writer/reader 186 are also generally local to one another but any combination of one or more of them could be remote from the others or they could all be remote from one another.

Array reader 160 may include a holder 161 which receives and holds an array unit 15, as well as a source of illumination (such as a laser) and a light sensor 165 to read fluorescent light signals from respective features on the array. Reader 160 can be any suitable apparatus for reading an array, such as one which can read the location and intensity of fluorescence at each feature of an array following exposure to a fluorescently labeled sample. An array reader 160 may be a scanner which scans one or more illuminating laser beams across each array in raster fashion and any detects any resulting fluorescent signals, such as described in U.S. Pat. No. 6,406,849. One such scanner that may be used for this purpose is the AGILENT MICROARRAY SCANNER manufactured by Agilent Technologies, Palo Alto, Calif. However, arrays may be read by any other method or apparatus than the foregoing, with other reading methods including other optical techniques (for example, detecting chemiluminescent or electroluminescent labels) or electrical techniques (where each array feature is provided with an electrode to detect hybridization at that feature in a manner disclosed in U.S. Pat. No. 6,251,685, U.S. Pat. No. 6,221,583 and elsewhere). Reader 160 also includes an identifier reader 163 to read an identifier, such as bar code 356, appearing on each array unit 15 to be read. Identifier reader 163 may automatically read each array identifier as that array is loaded into reader 160 or it may be a manually operated wand or the like which an operator passes over each identifier 356. The scanning components of scanner 160, holder 161, and reader 163 are generally all local to one another and may all be contained within the same housing of a single same apparatus.

FIG. 4 also illustrates a number of user stations 220a, 220b, 220c, each of which includes a display 228, communication module 224 having access to communication channel 180, and a processor 220 communicating and controlling display 228 and module 224. Only three user stations 220 are shown in FIG. 4. Any one or more of user stations 220 may be remote or local to the others or all may be remote or local. Similarly, any one or more (or all) of user stations 220 may be remote or local to the reading station 150.

Different users at user locations any of which may be remote or local to reading station 150, each receive one or more array units 15. Each user will typically expose each array 12 on the array unit 15 to a sample, for example a test sample derived from a human or other organism or source. Samples can be prepared for exposure to an array 15 using methods such as described in U.S. Pat. Nos. 6,235,483 or 6,132,997. Array washing and drying can be accomplished in a known manner. At some point the user will record the identifier 356 on the substrate 10 of the array unit 15 to which they exposed samples. This can be done either manually (for example, reading the bar codes with a bar code reader and writing down the bar code numbers) or with the aid of a processor (where the read bar codes are stored by the processor in a memory). Each user then forwards a package 340 to reader station for reading, each package containing at least one exposed array unit and optionally a portable memory 324a (such as a disk) in package 340a only. A "package" in this context is one or more array units optionally with other items, all held together (such as by a common wrapping or protective cover or binding). Normally the common wrapping will also be a protective cover (such as a common wrapping or box) which will provide additional protection to the substrate 10 from exposure to the external environment. In the case of just a single array unit the package may be that array unit with some protective covering over the array 12 and substrate 10 (which protective cover may or may not be an additional part of the array unit 15 itself).

The different packages 340a, 340b, 340c are received and opened from the different users. This opening may occur at reader station 150 or elsewhere (local or remote from reader station 150). Note that package 340a from one user includes the portable memory 324a while the others 340b, 340c each only respectively contain an array unit 15b, 15c.

Figure 5:
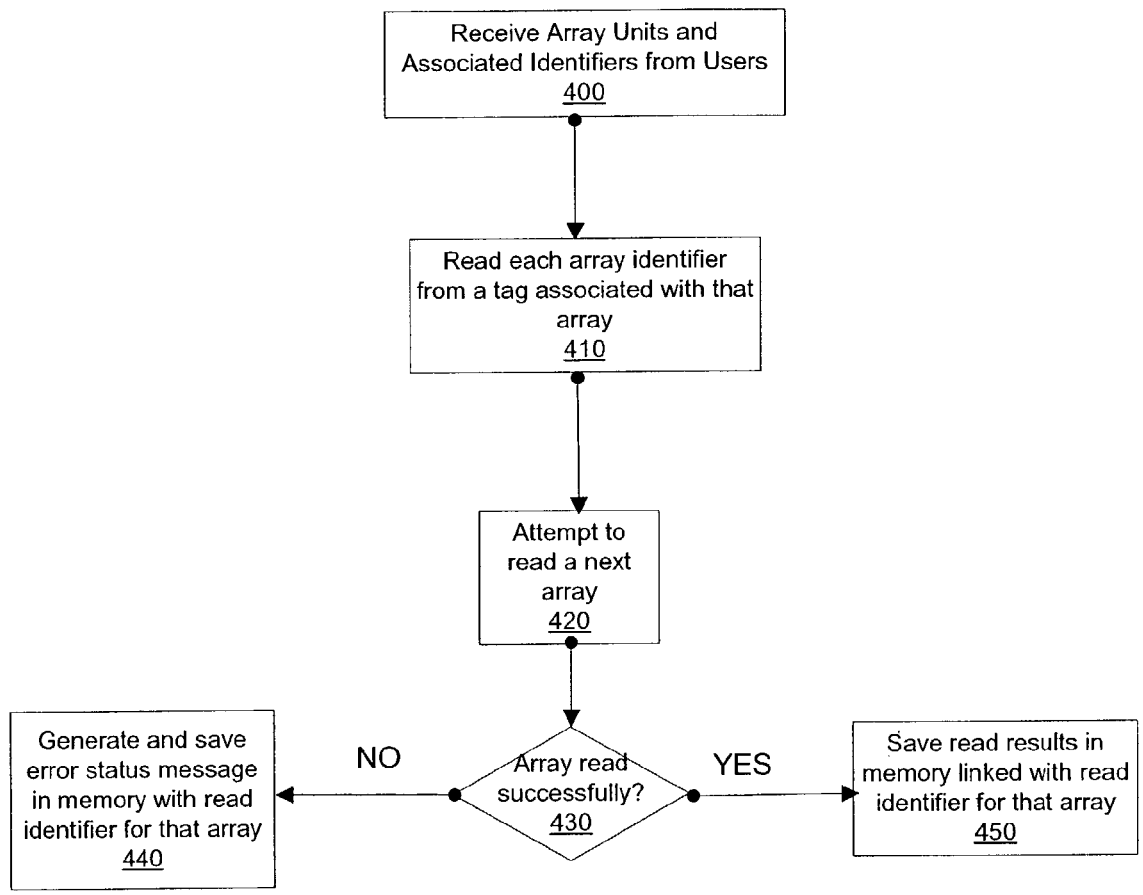
FIGS. 5 and 6 are flowcharts illustrating a method of the present invention.
Figure 6:
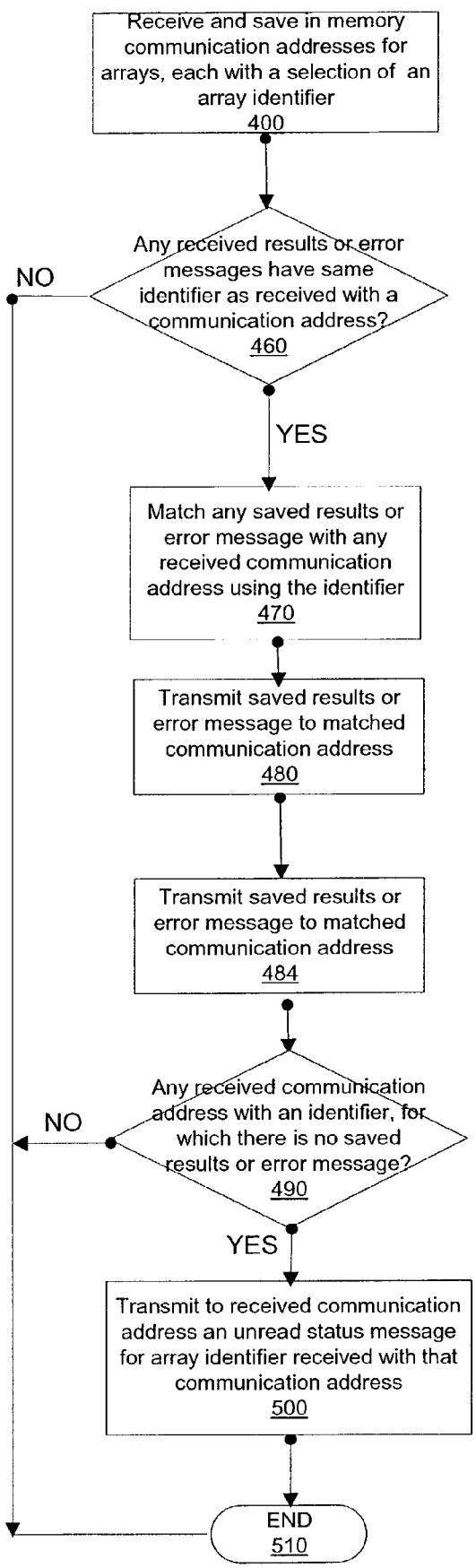

At reader station 150 the following events occur as illustrated particularly in FIGS. 5 and 6 (numbers in parentheses refer to events in FIG. 5 or 6). For simplicity it will be assumed that each array unit 15 carries just one array 12. However, the extension to the situation where one or more of the array units 15 carry more than one array 12 will be readily understood. Turning to FIGS. 5 and 6 in particular, each array unit 15 and associated identifier 356 is received (400) at reader station 150. Note that each array 12 is received with its associated identifier 356 by virtue of the identifier being on substrate 10 carrying that array 12. That is, each array 12 on array unit 15a are each associated with an identifier 356a, while each array 12 on array unit 15b is each associated with an identifier 356b, while each array 12 on array unit 15c is each associated with an identifier 356c. Each received identifier is then read (410) by identifier reader 163 from a tag associated with that array (which as mentioned may be reading of the bar codes 356a, 356b, 356c printed directly (or otherwise) on the substrate of respective array units 15a, 15b, 15c. Reader 160, under control of processor 160 then attempts to read (420) an array 12 on a received array unit 15a. This will be the array next in line for reading (which may just be a first one of the received arrays or otherwise). Array reader 160 may or may not be able to successfully read an array 12 (430). If unsuccessful an error message is generated by processor 162 and saved in memory 184 (440) linked with the read identifier 356a for that same array on array unit 15a. If successfully read then the read results are saved in memory 184 (450) linked with the read identifier for that same array on array unit 15a. The processor 162 then causes reader 160 to attempt to read the next array from array unit 15b then 15c in sequence, each time repeating the foregoing series of events 410 to 450. Note that results from reading an array reading may be raw results (such as pixel intensity values from the entire scanning of the array) or can be processed results, such as obtained by rejecting a reading for an array feature which is below a predetermined threshold and/or forming conclusions based on the pattern read from the array (such as whether or not a particular target sequence may have been present in the sample).

Simultaneously with events in FIG. 4, processor 162 also executes the events in FIG. 5 from time to time. In particular processor 162 receives through communication channel 180 and module 164, different communication addresses for arrays each along with a selection of an array identifier 356, and saves these in memory 184. Each communication address and identifier 356 received along with that communication address, can be received from a different user station 220. For example, user station 220a may transmit through communication channel 180 to processor 162 a first communication address (for user station 220a) along with a selection of identifier 356a for array unit 15a. Similarly, user station 220b may transmit through communication channel 180 to processor 162 a second communication address (for user station 220b) along with a selection of identifier 356b for array unit 15b. User station 220c may transmit through communication channel 180 to processor 162 a third communication address (for user station 220c) along with a selection of identifier 356c for array unit 15c. Of course, it will be understood that user station 220 may transmit the communication address for that user station 220 along with a selection of multiple array identifiers. In an alternative configuration, a communication address for user station 220a may be received at reader station 150 along with a selection of array identifier 356a from portable memory 324a read by writer/reader 186. Note that a "communication address" may be any way of identifying a station (such as any of stations 220) to which read results or status messages for a particular array should be transmitted over communication channel 180. For example, a communication address may be an electronic mail ("e-mail") address, Internet Protocol ("IP") address, telephone number, and the like.

As mentioned, the communication address is received along with a "selection" of an array identifier. This means that the array identifier(s) may itself actually be received along with the communication address (for example, by a user typing in the identifier(s) at a user station 220 or from memory 324a), or some other indication is received that a particular communication address should be linked with a particular array identifier (or array identifiers). For example, a user station 220 in communication with reader station 150 may simply receive in response to a sent query on what arrays have been read (or attempted to be read) at station 150, a list of array identifiers for all arrays attempted to be read. The user station may then simply select from the list (such as by pointing and clicking on the displayed identifier(s)) the array identifiers for which that user station wishes to receive read results or status information. In this case processor 162 automatically links the user communication address (such as an IP address automatically transmitted from the user station) with the selection of the array identifier(s).

From time to time processor 162 checks for any received reading results or error messages in memory 184, which have same the same identifier as in an identifier selection received along with a communication address (460). If there are none this routine ends 510. If there are one or more then processor 162 automatically matches (470) the saved results for each with one of the different communication addresses using the identifier, and automatically transmits (484) the saved results for those arrays to the matched different communication addresses. For example, if the first communication address has been received from user station 220a along with a selection of identifier 365a before reading of the array 12 of array unit 15a, and that array is later attempted to be read, processor 162 will in event 470 then automatically match the saved read results or error message for the array 12 of unit 15a, with the first communication addresses using the identifier, and automatically transmit the saved results or error message for that array to the first communication address. On the other hand the same automatic matching and transmission will occur if that array 12 of array unit 15a was attempted to be read before the communication address was received from station 220a along with the selection of identifier 356a.

Optionally, processor 162 also checks (490) if a communication address has been received with an identifier selection, for which identifier there is no saved results or error message. If NO then this routine ENDS 510. If YES then processor 162 transmits (500) to any such received communication address, an unread status message for array identifier received with that communication address. This unread message status may, for example, be a message such as "The array for which read results is requested has not yet been read by this station".

The results of the reading (processed or not) received at a location corresponding to a communication address, can be received there for further evaluation and/or processing, or use. This data may be transmitted by others as required to reach the location, and can be re-transmitted to elsewhere from that location.

Variations of the above embodiments are, of course, possible. For example, processor 162 may simply erase from memory a communication address received with a selection of an array identifier corresponding to an array which has not yet been attempted to be read (or which has been read following transmission of the read results or error message). In the case where an attempt to read the array has not yet been made, the inquiring user station 220 may simply have to repeat the inquiry from time to time. The user can easily configure their software at station 220 to accomplish this automatically. Alternatively, processor 162 may transmit to the inquiring user station 220 software code (for example, a java applet) which will automatically cause the software (for example, an internet browser) running on processor 162 to repeat the inquiry at an interval specified by the code.

In another variation an address other than a communication address can be used to which results from reading an array are to be sent. For example, the address may be a physical location address (such as a geographical address or street address). In this case, the read results for an array specified in a selected array address, may be forwarded in a physical embodiment to that address (for example, as data on a portable memory by mail or courier) at which they are received.

Also, processor 162, module 164, memory 184 and writer/reader 186 can all be separated from array reader 160 and reader 160 controlled by another processor and communication module (not shown) which can them communicate through channel 180 with processor 162. This is particularly true if processor 162, module 164, memory 180 and writer/reader 186 are all remote from array reader 160 or it is desired that they serve multiple array readers 150 over communication channel 180. Thus, the method of the present invention also contemplates simply: receiving results from reading each array with a linked read array identifier, saving each read array result in a memory linked to the array identifier; receiving different communications addresses and a selection of an array identifier for each; and for at least some of the arrays, matching the saved results for each with one of the different communication addresses using the identifier, and transmitting the saved results for those arrays to the matched different communication addresses.

In a further variation, the communication address may be received at the reader station 150 by being present in a tag itself. For example, each array user at each reader station 220 may save their communication address for an array to the same tag associated with that array which carries the array identifier (such as a memory attached to the array substrate). Thus, the tags for different array units 15 each can carry both the array identifier and the communication address for that array (with different array tags carrying different communication addresses). In this event, the communication address for an array can be read from the tag at reader station 150 along with the identifier for the same array (optionally both may be read with the identifier reader) and both saved in a memory linked to one another. The matching of the saved read results for an array can occur simply by saving the read results for an array linked with the communication address and identifier both read from the tag associated with that array. A received selected array identifier (such as received from a transmission from a remote location) can be used to automatically retrieve the saved read results and communication address for the identified array. The retrieved results are then automatically transmitted to the retrieved matched communication address.

Various further modifications to the particular embodiments described above are, of course, possible. Accordingly, the present invention is not limited to the particular embodiments described in detail above.

What is claimed is:
1. A method of processing biopolymer arrays, comprising:
    (a) reading a different array identifier for each biopolymer array from a tag associated with that array;
    (b) reading at least some of the biopolymer arrays and saving results from each read biopolymer array in a memory linked with the read identifier for that array;
    (c) receiving different communication addresses and a selection of an array identifier for each communication address;
    (d) for at least some of the read biopolymer arrays of step (b), matching the saved results for each array with one of the different communication addresses using the identifier, and transmitting the saved results for those arrays to the matched different communication addresses.

2. The method according to claim 1 wherein the biopolymer arrays are polynucleotide arrays.

3. The method according to claim 2 additionally comprising for at least some of the selection of array identifiers received in (c), transmitting status information on array reading to the communication address for each.

4. The method according to claim 2 wherein for at least some of the arrays, (c) occurs before (b) and the method additionally comprises:
    saving the different communication addresses and the selected array identifier for each in a memory;
    following reading and saving of results and read array identifiers in (b), then automatically performing the matching and transmitting of (d).

5. The method according to claim 2 wherein for at least some of the arrays (b) occurs before (c) and the method additionally comprises:
    following the receiving in (c), then automatically performing the matching and transmitting of (d).

6. The method according to claim 2 wherein the tag for each array is associated with the array by being carried by a substrate on which the array is located.

7. The method according to claim 2 wherein the tag for each array is associated with the array by being on or in a same package as the array.

8. The method according to claim 2 wherein the tag comprises a bar code.

9. The method according to claim 2 wherein the tag comprises an electrically readable memory.

10. The method according to claim 1 wherein the arrays are peptide arrays.

11. An array reading station for reading multiple biopolymer arrays comprising:
    (a) an identifier reader to read a different array identifier for each biopolymer array from a tag associated with that array;
    (b) an array reader to read arrays, which array reader may be the same or different from the identifier reader;
    (c) a memory unit;
    (d) a communications unit to receive and transmit data; and
    (e) a processing unit in communication with the identifier reader, array reader, and memory, and which executes the method of claim 1.

12. The array reading station according to claim 11, wherein the communications unit receives different communication addresses and a selection of an array identifier for each communication address, and wherein, for at least some of the selection of array identifiers received, the communication unit transmits status information on array reading to the communication address for each array identifier.

13. The array reading station according to claim 12 wherein for at least some of the arrays, the receiving occurs before the transmitting and:
    the different communication addresses and the selected array identifier for each are saved in the memory unit; and
    following reading and saving of results and read array identifiers, then the processor unit automatically performs the matching and transmitting.

14. The array reading station according to claim 12 wherein for at least some of the arrays the reading and saving of results occurs before the receiving and, following the receiving, the processor automatically performs the matching and transmitting.

15. A computer program product comprising a computer readable medium carrying a computer program code which performs the method of claim 2.

16. The computer program product according to claim 15 additionally comprising for at least some of the received selection of array identifiers, transmitting status information on array reading to the communication address for each.

17. The computer program product according to claim 15 wherein for at least some of the arrays (b) occurs before (c) and the method additionally comprises:
    following the receiving in (c), then automatically performing the matching and communicating of (d).

18. The computer program product according to claim 15, wherein the tag for each array is associated with the array by being carried by a substrate on which the array is located.

19. The computer program product according to claim 15, wherein the tag for each array is associated with the array by being on or in a same package as the array.

20. A method comprising transmitting a communication address and a selection of an array identifier for each, and receiving as a result of the method of claim 2 the results from reading the array specified by that array identifier.

21. A method of processing data from the reading of biopolymer arrays, comprising:
    (a) receiving results from reading each array with a linked read array identifier, and saving each read array result in a memory linked to the array identifier;
    (b) receiving different communications addresses and a selection of an array identifier for each communication address;
    (c) for at least some of the arrays, matching the saved results for each array with one of the different communication addresses using the identifier, and transmitting the saved results for those arrays to the matched different communication addresses.

22. The method according to claim 1, wherein said biopolymer arrays are addressable.

23. The method according to claim 1, wherein said reading of said biopolymer arrays comprises scanning an illumination source across said biopolymer arrays and detecting a fluorescent signal.

24. The method according to claim 1, wherein said communication address is for a local user station.

25. The method according to claim 1, wherein said communication address is for a remote user station.

* * * * *